United States Patent [19]

Nelson

[11] Patent Number: 5,300,060
[45] Date of Patent: Apr. 5, 1994

[54] BLOOD BAG SYSTEM FOR SEPARATION AND ISOLATION OF NEOCYTES AND GEROCYTES

[75] Inventor: Edward J. Nelson, San Rafael, Calif.

[73] Assignee: Miles Inc., Berkeley, Calif.

[21] Appl. No.: 772,402

[22] Filed: Oct. 7, 1991

Related U.S. Application Data

[63] Continuation-in-part of Ser. No. 364,756, Jun. 12, 1989.

[51] Int. Cl.$^5$ ............................................. A61M 5/00
[52] U.S. Cl. ..................................... 604/410; 604/403
[58] Field of Search ................................ 604/410, 4–6, 604/905, 406; 210/749, 767, 787

[56] References Cited

U.S. PATENT DOCUMENTS

| | | | |
|---|---|---|---|
| 3,870,042 | 3/1975 | Viguier | 604/410 X |
| 3,911,918 | 4/1975 | Turner | |
| 4,222,379 | 9/1980 | Smith | |
| 4,280,497 | 7/1981 | Warner et al. | |
| 4,416,778 | 11/1983 | Rogers | |
| 4,586,928 | 5/1986 | Barnes et al. | |
| 4,609,372 | 9/1986 | Carmen et al. | 604/262 |
| 4,767,541 | 8/1988 | Wisdom | |
| 4,786,286 | 11/1988 | Cerny et al. | 604/406 |
| 4,810,378 | 3/1989 | Carmen et al. | |
| 4,846,795 | 7/1989 | Minagawa | 604/410 |
| 4,857,190 | 8/1989 | Wada et al. | |
| 4,892,537 | 1/1990 | Carmen et al. | |
| 4,969,882 | 11/1990 | Carmen et al. | |
| 4,997,577 | 3/1991 | Stewart | 210/767 |
| 5,098,371 | 3/1992 | Juji et al. | 604/4 |
| 5,128,048 | 7/1992 | Stewart et al. | 210/749 |

Primary Examiner—Robert A. Hafer
Assistant Examiner—Sam Rimell
Attorney, Agent, or Firm—Elizabeth F. Enayati; James A. Giblin

[57] ABSTRACT

A generally flat, elongated edge-sealed polymeric blood bag having a length to width ratio of at least 2 to 1 and one end portion in tapering communication with a connected single tubing which in turn is in closed communication via a Y-connector with both a bag access port and at least one other Y-connector. The second Y-connector is in closed communication with at least one auxiliary bag, preferably two auxiliary bags. Once the upper neocyte portion is expressed from the elongated blood bag the lower, more dense gerocytes can be saved in the original elongated bag or expressed into another connected bag via the Y-connector assembly for subsequent use or storage. The bag system is especially useful for separating and isolating both components of a neocyte/gerocyte red blood cell mixture in an open system and for providing a means for saving the otherwise discarded gerocytes for subsequent use. A physiological solution can be introduced via the Y-connector assemblies into the elongated bag to reconstitute the dense gerocytes.

4 Claims, 4 Drawing Sheets

BLOOD BAG SYSTEM FOR SEPARATION AND ISOLATION OF NEOCYTES AND GEROCYTES

This application is a continuation-in-part of U.S. patent application Ser. No 364,756 entitled "Leukocyte-poor Red Blood Cell Storage System", filed 12 Jun. 1989.

BACKGROUND OF THE INVENTION

This disclosure is concerned generally with flexible plastic bags used for collecting, processing and storing blood and blood components. The disclosure is especially concerned with a blood bag system found useful for separating, isolating and storing both old and young red cells on the basis of their relative densities.

The manufacture and use of flexible, plastic containers, or bags, for the collection, processing and storage of blood and blood components is well known. Whole blood from a donor is typically obtained via venipuncture and collected via tubing in a donor bag. The donor bag may or may not be connected via tubing to one or more satellite or transfer bags.

When connected to at least one transfer bag, the donor/transfer bag combination is commonly referred to as a "multiple" blood bag system. Such a system may include one, two, or three transfer bags, all in sealed communication with the donor bag so that, once blood or blood components are introduced into the system, the whole blood or its components may be moved from one bag to another by external manipulation of valves, and the like, thereby avoiding or minimizing contamination. Such multiple bag systems are thus commonly referred to as "closed" blood bag systems. Multiple blood bag systems not in sealed communication with the donor bag, or designed for attachment to the donor bag following initial collection are generally referred to as "open" blood bag systems.

In a typical multiple blood bag application, whole blood is collected into a donor bag and all connected transfer bags, which are typically empty, are placed in a centrifuge cup designed to hold the filled donor bag in a generally upright position. The bag contents are then centrifuged to separate whole blood into its lighter plasma component and its heavier red blood cell component.

By manipulating a valve, which typically is a frangible valve within the system, the upper plasma may then be expressed into one of the transfer bags, possibly for further processing (e.g., into platelet-rich and platelet-poor components which may be expressed further into other connected transfer bags). The separated platelet-poor plasma component subsequently may be fractionated into a variety of other products useful in so-called component therapy, including clotting factors, immune serum globulins, albumin, and the like.

During the first separation of plasma from red blood cells in a centrifuged donor bag, the upper plasma portion is often removed from the donor bag using a relatively simple device known as a plasma expresser. The expresser simply squeezes the donor bag until the upper, less dense plasma is fully expressed out of the bag, typically into a connected transfer bag.

In U.S. Pat. No. 4,857,190 (Wada et al.), a blood bag for separating white blood cells from platelets is shown. In that disclosure, a conventional blood bag is modified at the bottom to provide a small receptacle for collection and isolation of white blood cells (WBCs) from a platelet/WBC mixture. That disclosure focuses on minimizing the interface between the separated platelets and WBCs by carefully controlling the volume and dimensions of the continuous receptacle and by providing a centrifuge insert adapted to accommodate the bag and receptacle.

In U.S. Pat. No. 3,911,918 (Turner), there is disclosed an hour-glass shaped plastic blood bag comprising several compartments for the separation and isolation of blood components. That bag is capable of being separated to form a number of individual storage compartments for the separated components following component separation. As pointed out in that patent, prior art blood storage containers previously had not been detailed in size and shape to contain a predetermined quantity of blood or a blood component, such as plasma, in separate compartments.

More recently in U.S. Pat. No. 4,416,778 (Rogers), there is disclosed a dual compartment plastic blood bag in which the two compartments are connected via a tubing. The tubing includes a valve adapted to open only after a given centrifugation force is obtained. The bag is said to be especially useful for separating less dense and relatively younger red blood cells (i.e., neocytes) from more dense and relatively older red blood cells (i.e., gerocytes). As pointed out in that patent, the teachings of which are incorporated herein by reference, the use of neocytes is thought to be useful in minimizing iron overload possibilities in patients who depend on repeated blood transfusions.

To date, the primary method used for separating various blood components is simple centrifugation using either conventional bags or specially designed blood bags or using a specialized mechanical apparatus. One apparatus useful for separating blood components, including neocytes and gerocytes, is an instrument known as an IBM Model 2991 blood cell separator.

Unfortunately, the bags and apparatus available for fine separation of blood components tend to be fairly complex and expensive, thus limiting their use. Various ways of providing simpler, less costly methods and devices for the separation and isolation of blood components, especially the separation of neocytes and gerocytes, have been investigated recently.

An elongated bag specifically designed for neocyte preparation is described in U.S. Pat. No. 4,892,537 (Carmen et al.). See also continuation U.S. Pat. No. 4,969,882 to the same inventors. That system does not provide a way for saving gerocytes for later use. Furthermore, in that system the supernatant is expressed along with the neocytes into the satellite bag, which results in a generally undesirable increase in total neocyte transfusion volume.

In practicing that patented system, the tubing leading from the donor bag to the elongated bag is often severed after both transfer of the RBC mixture into the elongated bag and centrifugation. The supernatant is then expressed out of the severed tube, and the remaining packed neocytes are transferred into the satellite bag. The remaining gerocytes are viscous and generally are not used. Thus, it is desirable to provide a self-contained system for introducing a diluting solution into the main bag to enable storage and subsequent use of gerocytes from a neocyte/gerocyte mixture.

SUMMARY OF THE INVENTION

The inventive blood bag system for the separation and isolation of both neocytes and gerocytes comprises a generally flat, elongated plastic bag which has a length to width ratio of at least about 2 to about 1 and a top end in tapering communication with a connected tubing. The tubing is in closed communication with at least one access port and at least one other bag. In a preferred embodiment, the tubing leading from the elongated bag is connected to a paired series of Y-connectors enabling communication with at least two other bags, one of which may contain a RBC preservative solution, as well as the tubing enabling introduction of the neocyte/gerocyte mixture into the elongated bag.

In practicing the inventive system, an RBC blood component mixture of neocytes and gerocytes is introduced into the first elongated bag. It should be noted that at this point, the mixture transfer is considered "open" unless done using a so-called "sterile connection" or "docking device". The tubing leading from the blood source to the elongated bag may include a filter for selectively filtering leukocytes from the neocyte/gerocyte mixture as it is introduced from the donor bag into the elongated bag. Alternatively, the tubing leading from the elongated bag to an auxiliary bag may include a similar filter for removing leukocytes as the neocytes are expressed into an auxiliary bag.

The mixture is then separated into neocyte and gerocyte components using conventional means, such as centrifugation. The weight of the neocytes to be separated is determined based on the weight and the hematocrit (HCT) of the original mixture. This neocyte weight typically is about 50% of total RBC mixture sample size by weight, and can range from between about 40% to 60%, depending on considerations such as blood availability, need for younger cells, and the like. The upper component, consisting of the separated neocytes and supernatant, is then expressed out of the tapered top of the bag which, when expanded by its contents, forms a funnel-like guide for directing the separated upper component from the bag and through the tubing in a substantially unobstructed manner.

In a preferred embodiment, the elongated bag has a volume of about 275 ml and a length to width ratio of at least about 2.5 to about 1. The bag has a pair of substantially parallel major sides, or edges, continuous with converging minor sides, or edges, defining an interior obtuse angle of at least about 110°, preferably about 145°. In a closed system, the elongated main bag is pre-connected or sterilely connected to the donor bag via a Y-connector assembly. In an open system the elongated main bag is connected to the donor bag via a spike located at the end of tubing extending from a Y-connector in communication with the elongated main bag.

In a preferred embodiment, the elongated bag is in closed communication with a first Y-connector assembly, including a Y-connector and appropriate tubing. One arm of the first Y-connector is in closed communication with a port access, while the other arm is in closed communication with a second Y-connector assembly. The second Y-connector of that assembly is in closed communication with at least one, preferably two, auxiliary blood bags. These bags may be used for receiving supernatant and/or neocytes expressed from the elongated bag. One auxiliary bag may contain a physiological solution or RBC preservative to be delivered into the elongated bag following neocyte expression to dilute the gerocytes and facilitate gerocyte expression from the bag. In another embodiment, one arm of the Y-connector of the second Y-connector assembly may provide access to additional Y-connector assemblies for a plurality of connections to additional satellite bags.

A preferred method of preparing gerocytes using the system of this disclosure involves obtaining a mixture of neocytes and gerocytes, together called packed RBCs, having a hematocrit of about 75% and being less than 4 days old. The packed RBCs are preferably filtered to remove at least 90%, preferably at least 99%, of any WBCs. The combination of neocyte and gerocyte cells are then weighed and centrifuged in the main bag to form an upper portion of neocytes and supernatant which are then expressed out of the bag, leaving concentrated gerocytes. An RBC preservative or other appropriate solution may be added to the gerocytes for storage, or a physiological solution may be added to dilute and enable expression of the gerocytes.

Details of our system and preferred variations are described in more detail below.

BRIEF DESCRIPTION OF THE FIGURES

FIG. 2 is a plan view of one preferred embodiment of the inventive blood bag system where three bags are used.

Like elements in each Figure have the same reference number.

DETAILED DESCRIPTION OF INVENTION

Figure 1:
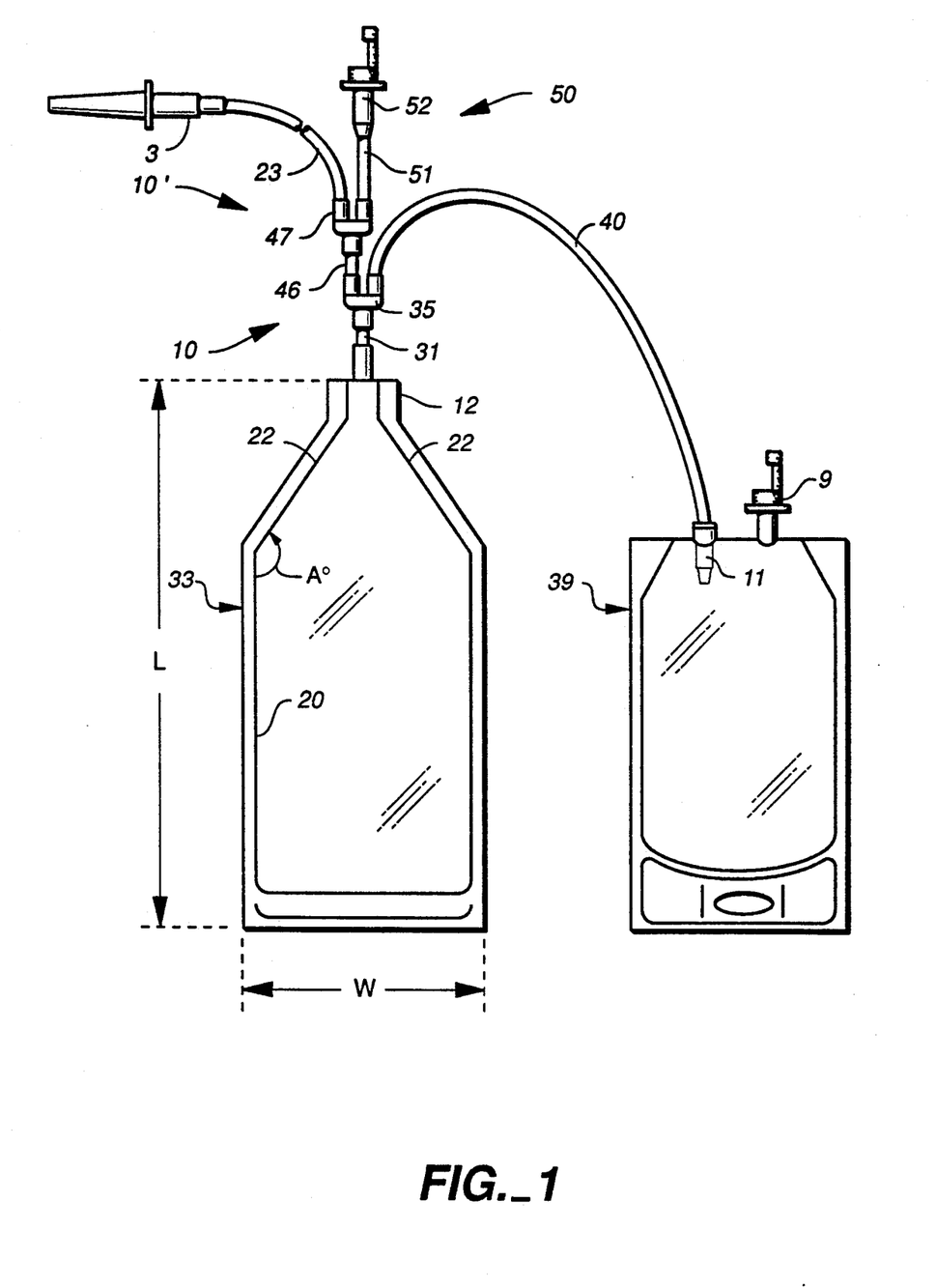
FIG. 1 is a plan view illustrating an exemplary neocyte/gerocyte blood bag system of this disclosure.
Figure 1A:
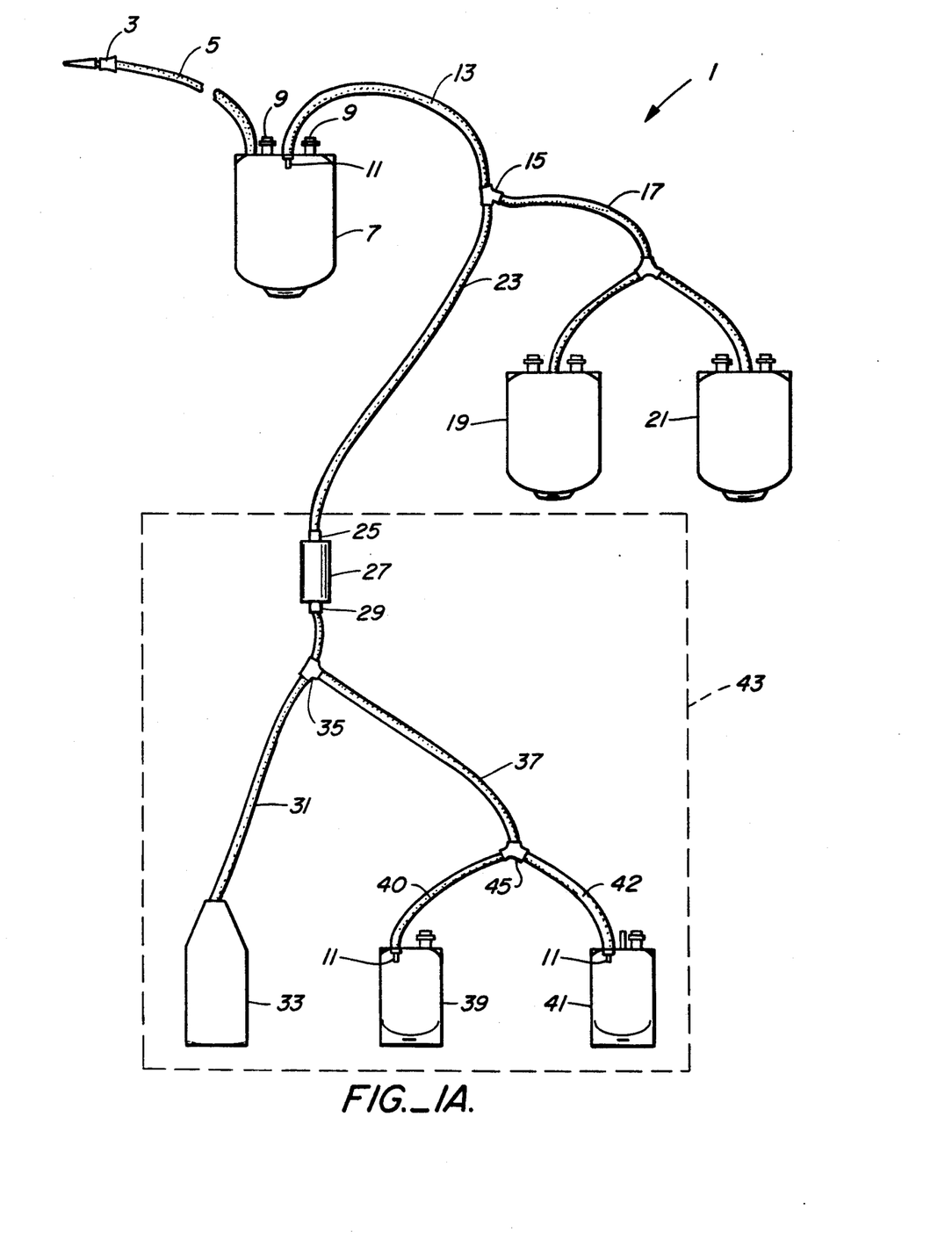
FIG. 1A shows a plan view of a very preferred embodiment of this disclosure, a key feature of which is enclosed within the dotted-line box 43.

As can be seen in FIG. 1A, one embodiment of the inventive system comprises a total of six bags of various types in closed communication with an intermediately located filter means.

The inventive system can be described in terms of its use and the various processing and storage steps which permit the preparation and long term storage of neocytes and, preferably, gerocytes.

Whole blood is drawn from a donor using a conventional phlebotomy needle 3. The blood is collected via conventional PVC tubing 5 into a conventional donor bag 7 which contains an anticoagulant such as citrate-phosphate-double dextrose. Bag 7 may be made of conventional blood bag film such as DEHP or TOTM plasticized PVC (e.g., see U.S. Pat. No. 4,222,379 Smith) and has a volume large enough to accommodate both the anticoagulant and a unit of donated whole blood (e.g. total volume for bag 7 is about 600 ml). Bag 7 typically includes one or more conventional blood bag port structures 9 and an internal frangible valve 11 such as that described in U.S. Pat. No. 4,586,928 (Barnes et al.). Such a frangible valve 11 is preferred and can also be seen in bags 39 and 41, described below.

In practicing the illustrated embodiment of FIG. 1A, after the plasma and RBC's are separated by centrifugation of bag 7, valve 11 is opened by external manipulation and the upper plasma is expressed via tubing 13 through the right side of Y device 15 through tubing 17 into bag 19. The plasma may include blood platelets. Tubing 17 may now be sealed and cut using conventional techniques leaving bag 19 containing the plasma and platelets still in closed communication with bag 21. The contents of bag 19 are centrifuged and the lighter platelet poor plasma is expressed into bag 21. Bags 19 and 21 are preferably made from a plastic film having a high gas transmissivity, such as TOTM (see, for example, U.S. Pat. No. 4,280,497 to Carmen et al., incorporated herein).

In the illustrated embodiment, after the plasma has been expressed from donor bag 7 to bag 19, a RBC concentrate remains in donor bag 7. After reconstitution, with a RBC preservative solution, already in the closed system such as the solution in bag 41 (which is also used to prime the filter 27), the RBC mixture (unseparated neocytes, gerocytes and leukocytes) is passed via tubing 13 through the left side of Y device 15 and tubing 23 into the first port 25 of filter 27 which is adapted to remove at least about 98% of WBCs from the mixture and can be like that of U.S. Pat. No. 4,767,541 (Wisdom) or U.S. Pat. No. 4,810,378 (Carmen et al.).

Filtration is preferably by gravity. The RBC's then pass from filter 27 through second port 29 past Y device 35 via tubing 31 into neocyte/gerocyte separation bag 33, very preferably of the elongated conventional funnel-ended type described in EPO Application No. 0,191,360. A conventional seal is made on the tubing between filter exit port 29 and Y device 35 and bags 33, 39 and 41 are detached. The bags are centrifuged as described in EPO Application 0,191,360 to form a cell-free upper layer (preservative solution plus residual plasma) and a lower layer of density-separated red cells (both neocytes and denser gerocytes). Approximately ½ volume of upper layer (preservative solution plus residual plasma) is expressed into bag 41. The remaining upper layer (preservative solution plus residual plasma) and about the upper ½ of the red cells (the less dense neocytes) are expressed into final neocyte storage bag 39 (about 200 mL volume). Preservative solution plus residual plasma in bag 41 is added back to bag 33 to reconstitute, or dilute, the remaining red cells (gerocytes). The reconstituted gerocytes are transferred bag to bag 41 for long term storage. The neocytes in bag 39 are capable of storage for up to 42 days, depending upon the storage solution used. An example of such a 42 day RBC storage or preservative solution is AS-3, described by Simon et al. (Transfusion 1987, 27:178–182).

An added bonus of this illustrated system is that the gerocytes (presently often simply discarded) are maintained in the closed system and also in a preservative solution. Uniquely, this is all accomplished within a closed blood bag system. Thus, the gerocytes are not wasted and can be used in cases where RBC age is not a concern (e.g. where RBC's of a given type are given in relatively small, non-recurring amounts and where iron overload is not a concern).

Figure 3:
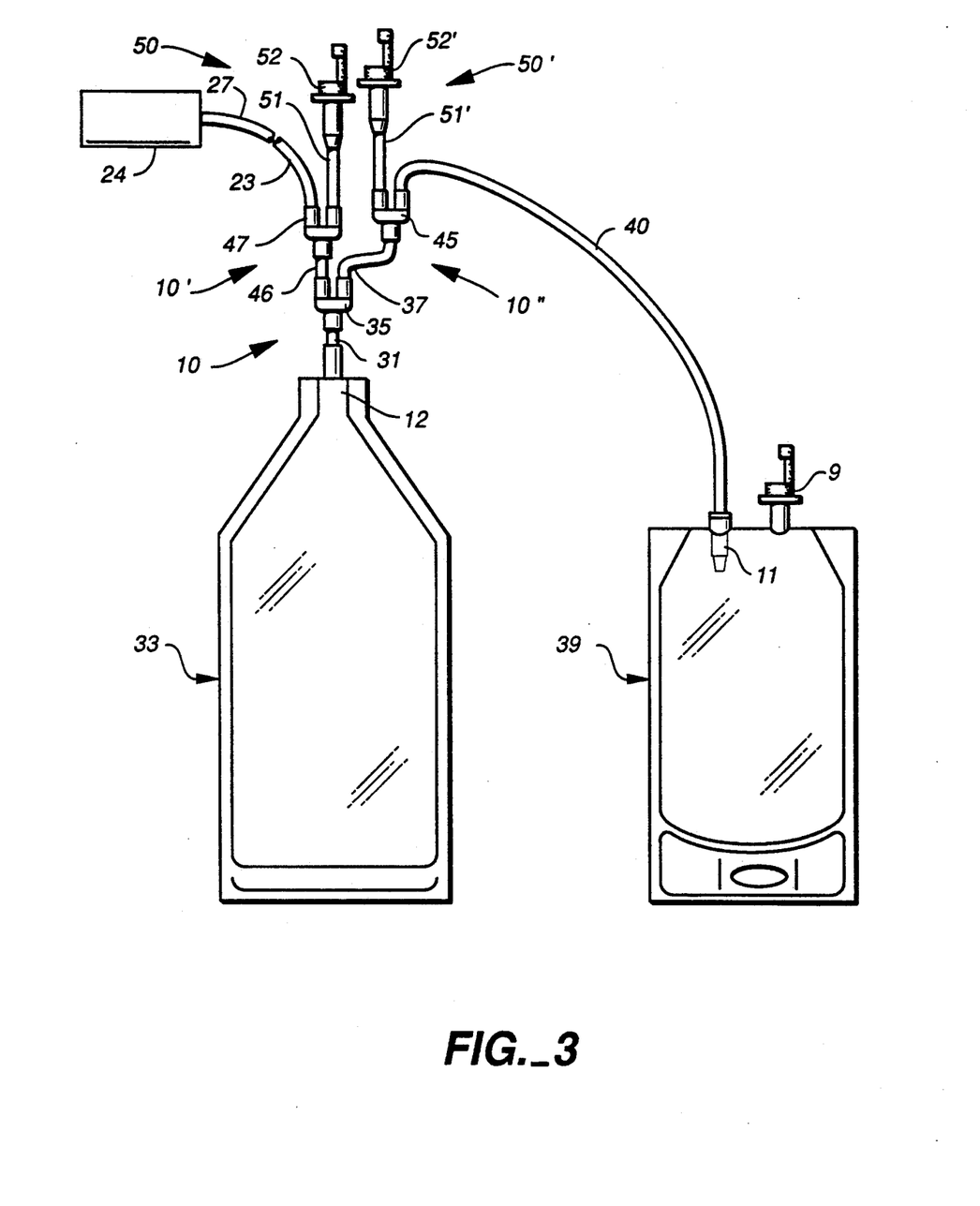
FIG. 3 is a plan view of an alternative blood bag system having a plurality of Y-connector assemblies that allows a port access for adding a RBC preservative or saline solution to the packed gerocytes of the first bag, and access for transfusion of the gerocytes.

A unique aspect of our closed system described above is shown within the dotted box 43 of FIG. 1A, and is shown in its various exemplary embodiments in FIGS. 1-3.

In an actual closed neocyte separation and storage method using our preferred system described in FIG. 1A, we were able to prepare neocytes from packed RBC's from which at least 98% of all WBC's were filtered out. In combination with the RBC storage solution (e.g. AS-3), these neocytes could be stored successfully for up to 42 days and still be used in a patient. These results are obtained because of the novel closed system of this disclosure.

Although a key feature of this disclosure is the subsystem within the dotted line box of FIG. 1A, a preferred system includes all components of that Figure, including pre-attached donor bag 7 and satellite bags 19 and 21. It can be appreciated, however, that a bag containing RBC's can be sterile docked into the sub-system within dotted line box 43 at, for example, a point on tubing 23 while still maintaining a closed system.

Unless otherwise indicated above, conventional blood handling techniques and materials can be used in making and using our novel system. All terms used (e.g. sterile, sterile connection, etc.) have their conventional meaning known to those skilled in the art. As used herein, RBC storage solution, RBC preservative solution and RBC additive solution are used interchangeably and should be considered equivalent.

Referring now to FIG. 1, main bag 33 is considerably elongated having a ratio of length (L) to width (W) dimensions of at least 2 to 1, preferably a ratio of about 2.5 to about 1. The bag 33 is substantially the same overall dimensions as that illustrated in U.S. Pat. No. 4,892,537 (Carmen et al.), the teachings of which are incorporated herein. The bag 33 includes substantially parallel major edges 20 comprising at least 50% of the bag length. These edges 20 are continuous with converging minor sides 22 which meet to form an interior obtuse angle A° that is at least about 110°, preferably about 145°. Converging edges 22 are designed to expand when the bag is filled and to guide the filled bag contents in a substantially unobstructed, funnel-like manner to exit port 12. Exit port 12 is continuous with a tubing 35a that is in closed communication with Y-connector 35.

In the embodiment of FIG. 1, exit port 12 communicates with the base of a conventional plastic 2-for-1 Y-connector 35 via tubing 31. The Y-connector 35 communicates at one arm with tubing 40 connected to satellite bag 39, which bag typically includes a sealed exit port 9. The Y-connector 35 communicates at the other arm with tubing 46. Tubing 46 communicates with a second conventional Y-connector 47 and spike tubing 23 and spike 3 through which the initial mixture of RBCs is introduced into main bag 33. In one embodiment, to maintain a totally "closed" system as described above, the RBC mixture (both neocytes and gerocytes) is introduced into main bag 33 via a pre-connected or sterilely connected Y-connector assembly 10. Otherwise, under current practice and when not processed under "closed" conditions, the useful cell component must be administered within 24 hours of introduction of the RBC mixture into the main bag 33.

One arm of the second Y-connector 47 of FIG. 1 may lead to a remote sealed port assembly 50. This assembly 50 includes a port element 52 and tubing 51. The port element 52 may be any commercially available port having a membrane enabling access to bag 39. Typically, such ports are adapted to receive conventional spike element 3, and are used to introduce preselected physiological solutions and/or expressing components, such as supernatant, gerocytes, or neocytes from the main bag 33.

The inventive bag system of FIG. 1 is suited for separating and saving the components of a neocyte-/gerocyte mixture (see below). The spike 3 connected to tubing 5 is adapted to be inserted into one of the exit ports of a conventional donor bag containing mixed red blood cells after the plasma has been expressed.

Auxiliary bag 39 is preferably also flat and may either be a conventional square bag or an elongated bag similar in size to main bag 33 so that when bag 33 is filled with mixed cells, empty and flat bag 39 may be wrapped around filled bag 33 for insertion into a centrifuge cup adapted to receive both in that manner. This assumes a somewhat cylindrical shape of filled bag 33 due to expansion. In one embodiment, a conventional valve may be associated with tubing 40 either externally, for example by a clamp, or internally, for example by a pierceable membrane, a frangible in-line pierceable, or a frangible valve. One such frangible internal valve 11 is illustrated in all Figures. Such valve 11 may close communication to bag 39 until the upper separated contents of bag 33 are ready for transfer to bag 39.

The ability to add solutions into the main bag 33 is perhaps the most distinguishing feature of this invention. As discussed above, prior art systems do not include sterile access to the main bag containing viscous gerocyte cells. As shown in the preferred embodiment of FIG. 2, the inventive blood bag system enables not only the selective removal of supernatant and neocytes, but also enables the reintroduction of supernatant or any other appropriate solution into main bag 33. In that illustrated embodiment, the main bag 33 is in closed communication with a first Y-connector assembly 10 consisting of tubing 31 and Y-connector 35. The main bag 33 is adapted to receive an RBC mixture from tubing 23 via one arm of Y-connector 35. The second arm of Y-connector is in closed communication with second Y-connector assembly 10', that includes tubing 37 and Y-connector 45. This second assembly 10', in turn, is in communication with auxiliary bags 39 and 41. Either auxiliary bag may contain a predetermined amount of RBC storage solution, saline solution, or the like.

In a preferred form of practicing the illustrated system, an RBC mixture is introduced into main bag 33, then the entire system is centrifuged. All or a portion of the resulting upper supernatant layer may be expressed into bag 39 via connector assemblies 10 and 10' and tubing 40. Any remaining supernatant layer plus the neocyte layer may then be expressed into bag 41 via connector assemblies 10 and 10' and tubing 42. A dense gerocyte layer remains in main bag 33. The expressed supernatant may then be returned from bag to main bag 33, again via tubing 40, to provide nutrition to the gerocytes for storage, and dilute, or reconstitute, the gerocytes for subsequent expression and use. The supernatant/gerocyte mixture may then be re-introduced into bag 39 along tubing 40 for storage and subsequent use.

FIG. 3 shows another embodiment of the inventive system having a plurality of Y-connector assemblies. The elements in FIG. 3 correspond to like elements of FIGS. 1 and 2. FIG. 3 has a third Y-connector assembly 10'', consisting of tubing 37 and Y-connector 45. That assembly 10'' may lead to one or more auxiliary bags, or may have a remote sealed port assembly 11'. In a similar fashion, the second assembly 10' may include a sealed remote port assembly 50. Other embodiments may include a preselected number of Y-connector assemblies, depending on the number of desired auxiliary bags and remote port assemblies as required for the particular use.

In practicing the method of the present invention, the following exemplary steps may be performed. First, about 275 ml of red blood cells of mixed age and approximately 70–80% hematocrit (HCT) are drawn into main bag 33 via tubing 23 using spike 3 or sterile connection to tubing 23. In a closed system, a filter 27 may be incorporated in the system between the blood source 24 (which source may be donor bag 7) and main bag 33. Empty bag 39 is wrapped about the filled bag 33 and both are inserted into a centrifuge cup insert about 63 mm in diameter and about 130 mm deep and generally conforming to the volume of the filled bag. Centrifugation proceeds at about 4000 x g for 30 minutes or until optimal separation of the desired cell components is achieved. The bag system is then removed and the upper supernatant and neocyte component is expressed from bag 33 into bag 39. Preferably, the supernatant is first expressed via port assembly 50 or 50' to an appropriate receptacle, e.g., a transfer bag. The neocyte component (with any residual supernatant) is then expressed into bag 39. To identify the amount of neocyte component to express, a calculation is made based on the weight of the upper component, as determined or calculated from the total weight of pre-separated red cells (i.e., the original unseparated RBC mixture), and the HCT. The amount of neocyte component expressed can readily be determined by one skilled in the art, taking into consideration such factors as whole blood availability, need to assure a relatively lower average age of the neocytes to minimize risk of iron overload, and the like. The neocyte component is then expressed using a conventional plasma expresser from bag 33 into bag 39 until the desired weight, as determined using the method described above, is transferred. Tube 40 is sealed and cut and bag 39 containing the neocyte fraction is then removed. At this point the expressed supernatant may then be reintroduced into bag 33 to dilute the remaining gerocytes for subsequent use.

Prior art systems require that the gerocytes are left in bag 33, without access to these gerocytes unless a sterile connection device is used. The addition of connector assembly 10' permits access to the gerocytes. A transfusion set can be attached to port assembly 50. In an alternative embodiment, the transfusion set can have a Y-connector to allow attachment of an auxiliary bag of saline or other similar solution.

Because the gerocytes are at a high hematocrit, they are viscous and do not flow readily. Thus, a saline solution can be added through port 52 to dilute the gerocytes to facilitate flow. The gerocytes can then be transfused through a transfusion set connected to port assembly 50. Alternatively, a second remote port assembly may be added via a Y-connector to tubing 51 or tubing 51', as shown in FIG. 3, such that saline may be added through one port. That port is then sealed off and the diluted gerocytes may then be stored and later transfused via the alternate port.

In one embodiment, a filter 27 may be included in tubing 38 or 42. In addition, illustrated embodiments shown in FIGS. 1–3 may include a filter 27 along tubing 23.

SEPARATION STUDIES

The above separation of neocytes from a mixed neocyte/gerocyte RBC population using a bag similar to bag 3 has already been described in U.S. Pat. No. 4,892,537, the teaching of which is incorporated herein by reference. Those data show that a satisfactory separation of younger (less dense) and older (more dense) cells is achieved with the blood bag system described in that patent. The separation compared favorably with the two techniques of using a mechanical cell separator and using a multi-chambered bag.

FIG. 2 shows a preferred embodiment of the system of this disclosure. As illustrated, a secondary solution 32, such as a red cell preservative solution or saline solution, may be contained in satellite bag 41. Alternatively, the solution 32 may be added to bag 41 via port 9 after removal of bag 39 containing the neocytes. After separation of the neocytes from the gerocytes, frangible valve 11 of bag 41 is opened to permit the secondary solution 32 to be added to the gerocytes in bag 33 via tubing 42. The diluted gerocytes are then transferred to bag 41 via tubing 42 for storage and ultimate transfusion through port 9.

Alternative ways to add the secondary solution 32 include introduction by either sterile connection to tubing 23, 40 or 42 or by adding a port to either tubing 23, 40 or 42 via a Y-connector and tubing as shown in FIG. 1. This would permit the addition of the secondary solution 32 to the gerocytes, which cells could then be transferred to bag 41 as mentioned above for storage and ultimate transfusion to a patient through port 9.

FIG. 3 shows yet another embodiment wherein a second port may be added to the system via a Y-connector attached either to tubing 23, 51, or 51'. Having two ports on the system permits secondary solution 32 to be added via one port and, after sealing off tubing to that port, subsequent storage of the gerocytes for later transfusion via the second port.

The embodiments of FIGS. 1-3 are particularly well-suited for use in open systems as discussed above. The configuration of Y-connectors permits such use, as contrasted with the closed system described in conjunction with FIG. 1A. While a closed system generally requires the inclusion of a filter to remove leukocytes from the neocyte/gerocyte cell mixture, a filter is not generally required in an open system. The omission of a filter element in the open system allows the expression and reintroduction of the supernatant as described in detail above.

Given the above disclosures, it is thought that numerous variations will occur to those skilled in the art. Accordingly, it is intended that the above described preferred system should be considered as illustrative and that the scope of the invention disclosed should be limited only by the following claims.

I claim:

1. A method of preparing both neocytes and gerocytes from a blood cell mixture containing some from the group consisting essentially of neocytes, gerocytes, and supernatant including plasma and preservative solution, the method comprising the steps of:
   a) obtaining the blood cell mixture in an elongated bag having a length to width ratio of at least about 2 to about 1,
   b) centrifuging the elongated bag containing the blood cell mixture to form a supernatant portion, a neocyte portion, and a gerocyte portion,
   c) expressing at least part of the supernatant portion from the elongated bag into a first auxiliary blood bag in closed communication with the elongated bag,
   d) expressing a predetermined fraction of the neocyte portion, from the elongated bag into a second auxiliary blood bag in closed communication with the elongated bag,
   e) transferring the expressed supernatant from the first auxiliary blood bag into the elongated blood bag to provide a suspension of the gerocytes; and
   f) transferring the gerocyte suspension from the elongated bag into the first auxiliary bag.

2. A method of preparing, from an initial mixture of red blood cells and white blood cells including leukocytes, both neocytes and gerocytes from a blood cell mixture containing some from the group consisting essentially of neocytes, gerocytes, and supernatant including plasma and preservative solution, the method comprising the sequential steps of:
   a) obtaining the blood cell mixture in an elongated bag having a length to width ratio of at least about 2 to about 1,
   b) filtering the initial mixture of red blood cells and white blood cells to remove the leukocytes,
   c) centrifuging the elongated bag containing the blood cell mixture to form a supernatant portion, a neocyte portion, and a gerocyte portion,
   d) expressing at least part of the supernatant portion from the elongated bag into a first auxiliary blood bag in closed communication with the elongated bag,
   e) expressing a predetermined fraction of the neocyte portion, from the elongated bag into a second auxiliary blood bag in closed communication with the elongated bag,
   f) transferring the expressed supernatant from the first auxiliary blood bag into the elongated blood bag to provide a suspension of the gerocytes; and
   g) transferring the gerocyte suspension from the elongated bag into the first auxiliary bag.

3. A method of preparing, from an initial mixture of red blood cells and white blood cells including leukocytes, both neocytes and gerocytes from a blood cell mixture containing some from the group consisting essentially of neocytes, gerocytes, and supernatant including plasma and preservative solution, the method comprising the sequential steps of:
   a) obtaining the blood cell mixture in an elongated bag having a length to width ratio of at least about 2 to about 1,
   b) centrifuging the elongated bag containing the blood cell mixture to form a supernatant portion, a neocyte portion, and a gerocyte portion,
   c) expressing at least part of the supernatant portion from the elongated bag into a first auxiliary blood bag in closed communication with the elongated bag,
   d) filtering a predetermined fraction of the neocyte portion, which may include residual supernatant, by expressing that portion from the elongated bag into a second auxiliary blood bag in closed communication with the elongated bag through a filter element,
   e) transferring the expressed supernatant from the first auxiliary blood bag into the elongated blood bag to provide a suspension of the gerocytes; and
   f) transferring the gerocyte suspension from the elongated bag into the first auxiliary bag.

4. A method of preparing both neocytes and gerocytes from a blood cell mixture containing some from the group consisting essentially of neocytes, gerocytes, and supernatant including plasma and preservative solution, the method comprising the steps of:
   a) obtaining the blood cell mixture in an elongated bag having a length to width ratio of at least about 2 to about 1, b) centrifuging the elongated bag containing the blood cell mixture to form a supernatant portion, a neocyte portion, and a gerocyte portion,
c) expressing at least part of the supernatant portion from the elongated bag,
d) expressing a predetermined fraction of the neocyte portion from the elongated bag into a first auxiliary blood bag in closed communication with the elongated bag,
e) introducing a sufficient amount of the supernatant portion from a second auxiliary blood bag into the elongated blood bag to provide a suspension of the gerocytes; and
f) expressing the gerocyte suspension from the elongated bag into the second auxiliary bag.

* * * * *